United States Patent [19]

Springer

[11] 4,329,368

[45] May 11, 1982

[54] PROCESS FOR PRESERVATION OF STORED WOOD CHIPS

[75] Inventor: Edward L. Springer, Madison, Wis.

[73] Assignee: The United States of America as represented by the Secretary of Agriculture, Washington, D.C.

[21] Appl. No.: 47,172

[22] Filed: Jun. 8, 1979

[51] Int. Cl.$^3$ .................. A01N 33/18; A01N 35/02
[52] U.S. Cl. ................................ 424/334; 424/348
[58] Field of Search .............................. 424/334, 348

[56] References Cited

U.S. PATENT DOCUMENTS

| | | | |
|---|---|---|---|
| 3,646,196 | 2/1972 | Springer et al. | 424/162 |
| 4,045,554 | 8/1977 | Springer | 424/164 |
| 4,125,628 | 11/1978 | Goldhaft et al. | 424/329 |

OTHER PUBLICATIONS

Chemical Abstracts 81:171706m (1976).
Springer et al., "Proceedings of the Complete Tree Utilization of Southern Pine Symp.", pp. 216-223 (8/78).

*Primary Examiner*—Leonard Schenkman
*Attorney, Agent, or Firm*—M. Howard Silverstein; David G. McConnell

[57] ABSTRACT

A process which inhibits the loss of wood substance, tall oil and chip brightness in wood chips during storage. The process involves treating wood chips with a dilute aqueous solution of formaldehyde and a phenol. This treatment effectively prevents the evolution of heat from the chips and microbial growth and thus limits chip deterioration and brightness loss while preserving tall oil. The process is also effective in preserving other moist plant-derived raw materials.

2 Claims, 1 Drawing Figure

PROCESS FOR PRESERVATION OF STORED WOOD CHIPS

BACKGROUND OF THE INVENTION (1) Field of the invention

This invention relates to the preservation of moist plant-derived raw materials. More particularly the invention relates to the preservation of wood substance, inherent tall oil and brightness in wood chips during stockpiling.

(2) Description of Prior Art

Outside storage of wood chips was introduced in the early 1950's because of the need to stockpile chips produced from sawmill and veneer plant residues. When the economic advantages of handling wood as chips became apparent, many pulpmills begain stockpiling chips instead of storing wood as logs. Although it is cheaper and easier to handle and store wood in the form of chips, increased wood deterioration occurs during outside chip storage. Wood chips lose more wood substance, tall oil and brightness during storage than do logs.

One principle difference between piled log and piled chip storage is that a significant amount of heat is evolved in piled chips. Center temperatures in chip piles frequently reach and remain near 150° F., thus resulting in deterioration of the material.

Heat production is caused by enzymatic respiration of living wood cells, respiration of rapidly multiplying populations of bacteria and fungi and direct chemical oxidation. Prevention of the heat release from bacteria, fungi, and living wood cells would stop the initial temperature rise and prevent the direct chemical reactions from releasing any significant amount of heat.

Chemical treatments for preventing chip deterioration should stop or reduce the initial heat evolution by inhibiting the respiration of living wood cells and the respiration of all present bacteria and fungi. A treatment that kills the wood cells, bacteria and fungi would be highly effective. The treatment must remain effective for long periods of time since reinnoculation of the chips by airborne microorganisms will be constantly taking place. Any chemical treatment should be effective for a considerable length of time and its cost should be less than the losses incurred from chip deterioration. It should be compatible with the pulping process, should not cause pollution and should not be hazardous to personnel who handle and apply it.

One method found to be effective in reducing wood substance losses in stored wood chips by limiting the effect of wood-destroying fungi, is described in U.S. Pat. No. 3,646,196. This method, using kraft green liquor, inherently produces a large reduction in wood brightness and has little favorable effect on tall oil retention.

Another method uses sodium bisulfite and various phenols and is described in U.S. Pat. No. 4,045,554. These treatments are effective against all three major effects of deterioration, i.e., wood substance, tall oil and brightness losses. One disadvantage of these treatments is that the sodium bisulfite component is very corrosive to steel and most types of stainless steel. Another disadvantage is that the most effective phenol when used together with sodium bisulfite is 2,4 dinitrophenol which is very toxic to humans and to animals.

Formaldehyde has been used as a preservative for moist plant and animal-derived materials, and is effective for only a few weeks according to the inventor's tests. Phenolic compounds such as para-nitrophenol have also been used to preserve moist plant derived materials. However, they are ineffective in reducing heat evolution in stored wood chips.

SUMMARY OF THE INVENTION

The invention is a method for preserving wood substance, tall oil, and brightness in stored wood chips, by treating the chips with an aqueous solution containing from 1.0 to 2.0 percent formaldehyde and from 0.40 to 0.80 percent para-nitrophenol.

It is also a method for retarding deterioration in cereal straws, reeds, corn stover, kenaf, sugar cane bagasse, and wood, by treating the material with an aqueous solution containing from 1.0 to 2.0 percent formaldehyde and from 0.40 to 0.80 percent para-nitrophenol.

The primary object of this invention is to provide a chemical treatment to reduce losses in wood substance, tall oil and chip brightness in wood chips during long-term storage. Another object is to provide a chemical treatment for preservation of all moist plant-derived materials. A further object is the provision of a chemical treatment for inhibiting the growth of bacteria, molds and fungi, and the respiration of wood cells in stockpiled wood chips. A still further object is to provide a chemical treatment for preservation of wood chips and other moist plant-derived materials which is simple, economical, long-lasting, and safer and less corrosive than other chemical methods. The method is simpler, quicker, and more effective than mechanical methods.

DESCRIPTION OF THE PREFERRED EMBODIMENTS

Figure 1:
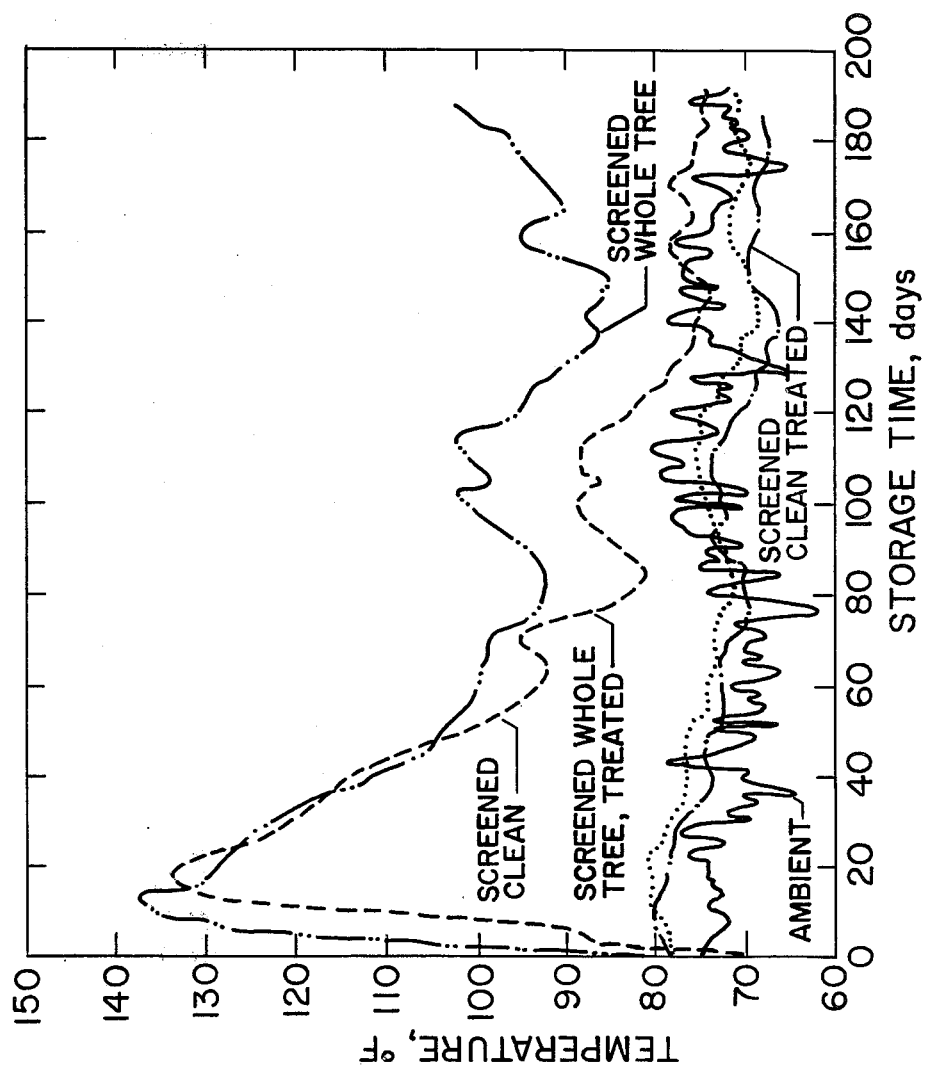

This invention provides a chemical treatment for the preservation of moist plant-derived materials. It combines two known biocides into a synergistic preservative treatment which has long-term effectiveness and which far surpasses in effectiveness either of the biocides individually or what one skilled in the art would have expected their combined effectiveness to be. Exemplifying the material with which the treatment is effective is wood chips. The treatment is also effective when used with cereal straws, reeds, corn stover, kenaf, sugar cane bagasse and other carbohydrate-based or ligno-cellulosic materials. The treatment comprises a dilute aqueous solution of formaldehyde and para-nitrophenol and was found to be highly effective in stopping heat evolution and deterioration in stored wood chips. It was discovered that this combination produces a strongly synergistic biocidal effect and kills or inhibits the growth of bacteria and fungi on treated chips and also kills the living wood cells or effectively inhibits their respiration. The synergistic biocidal effect remains operative for long periods of time. Treatment of the chips, or other material, can be accomplished by spraying, immersing, or any other means available for applying the solution onto the material. The treatment level is determined by the uptake of the treating solution and the percentages of formaldehyde and para-nitrophenol in the solution.

To further illustrate this invention, the following examples are given:

EXAMPLE I

The effect of potential control chemicals in inhibiting the growth of bacteria, molds and fungi on moist wood chips was studied by placing treated chips in sterilized glass jars topped with filter paper lids and holding the jars in a high-humidity room until growth of microorganisms was observed on the chips. For purposes of comparison, chips treated with water only were placed in some of the jars.

Sterilized one-quart Mason jars were used. A 1-inch-thick cellulose sponge was placed in the bottom of each jar. Water to humidify the air and thus keep the chips from drying was added to the jar so as to almost cover the sponge. Three 4-dram shell vials (21×70 mm) were placed horizontally on the sponge to support a 0.040 inch thick polypropylene sheet which prevented the chips from contacting the water. The test chips were supported by the polypropylene sheet. The steel lid of the jar was replaced by two circles of No. 597 Schleicher and Schuell filter paper (7 cm diameter), which permitted the chips access to air.

The jars, filled with about 100 grams of treated chips, were stored in an 80° F.-90% relative humidity room and monitored weekly for growth of microorganisms. The weeks elapsed to first detected growth of microorganisms in each jar was determined.

Batches of chips were treated by placing fresh chips in a nylon mesh bag and immersing them for 15 seconds in the treating solution. The chips were allowed to drain in the bag for about 2 hours before being thoroughly mixed and then placed in the jar.

To illustrate the synergistic effect of the formaldehyde and para-nitrophenol mixture, three separate batches of fresh slash pine chips were treated by immersion: one in a 1.00 percent formaldehyde solution, one in a 0.40 percent para-nitrophenol solution and one in a solution containing 1.00 percent formaldehyde and 0.40 percent para-nitrophenol. Each type of treated chips was subsequently placed in a test jar. For purposes of comparison another batch of chips was treated by immersion in water. The test results are shown in Table 1.

TABLE I

Storage times until observed growth of microorganisms on water-treated and chemically-treated slash pine chips stored in humidified and aerated glass jars (immersion treatment)

| Trial no. | Treatment | Concentration of chemicals in treating solution Pct | Weeks to observe growth of microorganisms |
|---|---|---|---|
| 1 | Water | — | 1 |
| 2 | Formaldehyde | 1.00 | 3 |
| 3 | P-Nitrophenol | 0.40 | 6 |
| 4 | Formaldehyde + P-Nitrophenol | 1.00 0.40 | 12 |

After only 1 week of storage, many microorganisms were present on the water-treated control chips. Visible microorganisms were present on the formaldehyde-treated chips after 3 weeks and on the para-nitrophenol-treated chips after 6 weeks. Chips treated with the mixture remained free of visible microorganisms until 12 weeks of storage. The mixture was thus much more effective than what would have been expected from the sum of the effects of the individual chemicals.

EXAMPLE II

The influence of potential control chemicals on the evolution of heat from fresh wood chips was studied by placing treated chips in insulated boxes and observing the temperature profiles at the center of the samples. In addition to temperature, carbon dioxide evolution was observed and chip brightness and quantity of microorganisms present after 90 days storage were visually estimated. The boxes, constructed of polystyrene foam, had an internal volume of 3.9 cubic feet or 0.11 cubic meters (inside dimensions 22½ by 13½ by 22 in. or 57 by 34 by 56 cm) with a wall thickness of 2½ inches or 6.4 centimeters. Each box was fitted with an inlet and outlet manifold and was fed water-saturated air at ambient temperature at a measured rate. Copper-constantan thermocouples, placed in the center of the chip mass, were used to measure temperatures. Because temperature profiles of untreated or water-treated chips cannot be satisfactorily duplicated, presumably because of changes in the wood with time, a water-treated control sample was separately run with every treated sample.

Fresh aspen chips were immersed for 10 minutes in a 1.0 percent solution of formaldehyde and were then drained for 2 hours. They were removed from the mesh bags and placed in an insulated box. This procedure was repeated using a 0.50 percent para-nitrophenol solution, and also with a solution containing 1.0 percent formaldehyde and 0.45 percent para-nitrophenol. Test results are given in table II.

The treatment with 1.00 percent formaldehyde solution completely stopped the initial heating and carbon dioxide evolution. Some heating and carbon dioxide evolution was, however, beginning to occur during the last month of storage. At that time, the treated chips were somewhat brighter but contained more microorganisms than the water-treated control chips.

Treatment of aspen chips with 0.50 percent para-nitrophenol solution had only a very small effect on heat and carbon dioxide evolution from the chips and no effect on brightness and quantity of microorganisms after storage.

The combination treatment with the solution containing 1.00 percent formaldehyde and 0.45 percent para-nitrophenol was highly effective: no carbon dioxide evolution and very little heat evolution were observed. At the end of storage the treated chips were much brighter than the water-treated control and contained no microorganisms. As can be seen from Table II, the preservative effects of the combined treatment were much greater than would have been expected from adding the preservative effects of the individual chemicals. The test results given in Examples I and II, therefore, illustrate the synergistic preservative effect of mixtures of formaldehyde and para-nitrophenol.

TABLE II

Comparison of water-treated controls with chemically-treated aspen chips stored for 90 days in 4 cubic foot insulated boxes ventilated with moist air (immersion treatment)

| Trial no. | Treatment | Concentration of chemicals in treating solution Pct | Chemical pickup Lb/ton O.D. wood | $CO_2$ evolved In 28 days Lb | $CO_2$ evolved In 56 days Lb | Time to reach maximum temperature Days | Maximum temperature °F. | Ambient temperature °F. | Brightness[1] after storage | Microorganisms[2] after storage |
|---|---|---|---|---|---|---|---|---|---|---|
| 1 | Water | — | — | 0.93 | 1.44 | 7 | 89 | 75 | | |
|   | Formaldehyde | 1.00 | 6.3 | 0.00 | 0.04 | 81 | 78 | 75 | + | — |
| 2 | Water | — | — | 0.43 | 0.59 | 6 | 80 | 67 | | |
|   | P-Nitrophenol | 0.50 | 2.2 | 0.34 | 0.40 | 7 | 79 | 67 | 0 | 0 |
| 3 | Water | — | — | 0.65 | 0.77 | 7 | 80 | 68 | | |
|   | Formaldehyde | 1.00 | 4.8 | | | | | | | |
|   | + P-Nitrophenol | 0.45 | 2.1 | 0.00 | 0.00 | 73 | 70 | 68 | ++ | +++ |

[1]Brightness scale:
+++ very bright;
++ much brighter than control;
+ brighter than control;
0 same as control;
− less bright than control.
[2]Microorganism scale:
+++ none present;
++ very few;
+ fewer than on control chips;
0 same as on control chips;
− more than on control chips.

EXAMPLE III

Further evaluation of a formaldehyde/para-nitrophenol mixture was carried out in chip pile simulators.

Separate batches of fresh loblolly pine whole-tree chips and clean debarked chips were each immersed for about 15 seconds in aqueous solutions containing 2.0 percent formaldehyde and 0.80 percent para-nitrophenol. Both types of chips were screened prior to treatment and in each case the fraction passing through a 1¼-inch top screen and retained on a ¼-inch bottom screen (both with square openings) was used. The chemical pickup of each type of chips is given in table III.

TABLE III

Data on chemical treatment of loblolly pine chips for storage in chip pile simulators

| Type of chips | Treatment | Solution concentration Pct | Chemical pickup of ovendried wood Pct | Weight of chemical of ovendried wood Lb/ton |
|---|---|---|---|---|
| Screened whole-tree | Formaldehyde | 2.0 | 0.66 | 13 |
|  | P-Nitrophenol | 0.80 | 0.26 | 5.3 |
| Screened clean | Formaldehyde | 2.0 | 0.34 | 6.8 |
|  | P-Nitrophenol | 0.80 | 0.14 | 2.7 |

The treated chips were placed in chip pile simulators, 16-foot-high cylinders with 4-foot diameters. Each has a 6-mil polyethylene liner and is insulated with 6 inches of fiberglass insulation (see Springer, et. al., "Evaluation of chemicals for preserving wood chips using pile simulators," p. 125, Tappi 56(6), June 1973). Untreated chips of both types were placed in identical simulators. Water-saturated air was fed to the bottom of each simulator at a rate of 2 cubic feet per hour or about 0.25 empty simulator volume per day. All chips were stored in the simulators for 6 months. Temperature at the center of the simulators was observed using copper-constantan thermocouples.

FIG. 1 shows the temperatures observed during storage at the geometric centers of the simulators filled with treated and untreated chips. For both clean debarked and whole tree chips, the treatment was highly successful in suppressing heating throughout the storage period. Table IV gives the losses in ovendried wood substance at various locations in the simulators at the end of 6 months storage.

TABLE IV

Loss in ovendry wood substance of untreated and chips after 6 months in simulators

| Sample location Vertical (from bottom) Ft | Cross section (from center) Ft | Sample size Kg | Weight loss (percent) Screened whole-tree | Screened clean | Screened whole-tree, treated* | Screened clean, treated* |
|---|---|---|---|---|---|---|
| 8 | 0 | 0.15 | 9.6 | 4.1 | 1.4 | 0 |
|  | 1 | 0.15 | 3.2 | 4.0 | 1.1 | 2.0 |
|  | 2 | 0.15 | 9.9 | 5.8 | 2.1 | 1.3 |
| 10 | 1 | 8 | 8.1 | 4.8 | 0.4 | 0 |
| 12 | 0 | 0.15 | 16.5 | 5.0 | 1.5 | 1.3 |
|  | 1 | 0.15 | 10.7 | 5.0 | 0 | 0 |
|  | 2 | 0.15 | 13.8 | 1.3 | 1.7 | 0.8 |

*Corrected for chemical pickup

Randomly selected samples of the initial untreated, unstored chips and samples of treated and untreated chips from the large sample bags after storage were subjected to kraft pulping. Screened whole-tree chips were pulped under the following conditions:

Active alkali—19.0 percent
Sulfidity—25.0 percent
Liquor to wood ratio—4:1
Time from 80° C. to 170° C.—90 minutes
Time at 170° C.—75 minutes For screened clean chips 17.5 percent active alkaki was used and all other conditions were the same as for the whole-tree chips. Overall pulp yields at Kappa number 50 (including wood losses during storage) for the initial and the stored chips are given in Table V.

TABLE V

Overall pulp yields at Kappa number 50 (percent)

| | Initial Pct | Six months storage | |
|---|---|---|---|
| | | Untreated Pct | Treated Pct |
| Screened whole-tree | 45 | 42 | 45 |
| Screened clean | 49 | 47 | 49 |

Untreated whole-tree chips suffered a 3 percentage point yield loss during storage whereas treated chips sustained no loss. Untreated clean chips showed a 2 percentage point yield loss and again the treated chips suffered no loss. For both types of chips, there were no significant differences in pulp strength between the initial and the treated, stored chips. However, the untreated, stored chips in both cases suffered a 20 percent drop in tear strength. Other strength values remained unchanged.

A representative sample of black liquor from each kraft cook was analyzed for tall oil by the method of Saltsman and Kuiken. The results are given in Table VI. The stored untreated chips lost more than 80 percent of their tall oil content, whereas, the stored, treated chips retained 85 percent or more of their tall oil.

All of the simulator test results indicate that the formaldehyde, para-nitrophenol mixture is highly effective in preserving stored wood chips.

TABLE VI

Tall oil in unstored chips and in untreated and treated chips after 6 months storage in simulators

| | Tall oil | | |
|---|---|---|---|
| Type of chips | Percentage of ovendried wood Pct | Weight of ovendried wood Lb/ton | Percentage of unstored retained Pct |
| Unstored | | | |
| Screened whole-tree | 2.1 | 43 | — |
| Screened clean | 1.5 | 29 | — |
| Stored | | | |
| Screened whole-tree | 0.28 | 6 | 13 |
| Screened clean | 0.28 | 6 | 19 |
| Screened whole-tree, treated | 1.8 | 36 | 85 |
| Screened clean, treated | 1.5 | 29 | 100 |

Having thus disclosed my invention, I claim:

1. A method for preserving wood substance, tall oil and brightness in stored wood chips comprising treating said chips with a biocidally effective amount of an aqueous solution containing from 1.0 to 2.0 percent formaldehyde and from 0.40 to 0.80 percent para-nitrophenol.

2. A method for retarding deterioration in cereal straws, reeds, corn stover, kenaf, sugar cane bagasse, and wood, comprising treating the material with an aqueous solution containing from 1.0 to 2.0 percent formaldehyde and from 0.40 to 0.80 percent para-nitrophenol.

* * * * *